United States Patent
Lee et al.

(10) Patent No.: US 9,631,207 B2
(45) Date of Patent: Apr. 25, 2017

(54) SIMULTANEOUS PRETREATMENT AND SACCHARIFICATION OF BIOMASS USING FUNGAL CONSORTIUM AND METHOD OF PREPARING BIOFUEL USING THE SAME

(71) Applicants: Konkuk University Industrial Cooperation Corp., Seoul (KR); Korea University Research and Business Foundation, Seoul (KR)

(72) Inventors: Jung-Kul Lee, Seoul (KR); Yun Chan Kang, Seoul (KR); Saurabh Dhiman, Seoul (KR); Jinglin Li, Seoul (KR); Ramakrishnan Ranjitha, Seoul (KR); Sigdel Sujan Chandra, Seoul (KR)

(73) Assignees: KONKUK UNIVERSITY INDUSTRIAL COOPERATION CORP., Seoul (KR); KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 0 days.

(21) Appl. No.: 14/750,502

(22) Filed: Jun. 25, 2015

(65) Prior Publication Data
US 2016/0312248 A1 Oct. 27, 2016

(30) Foreign Application Priority Data

Apr. 21, 2015 (KR) .................. 10-2015-0056209

(51) Int. Cl.
| | |
|---|---|
| C12P 19/02 | (2006.01) |
| C12P 19/04 | (2006.01) |
| C12N 9/42 | (2006.01) |
| C12P 7/06 | (2006.01) |
| C12P 7/10 | (2006.01) |
| C12P 7/12 | (2006.01) |
| C12P 19/14 | (2006.01) |
| C12P 19/12 | (2006.01) |

(52) U.S. Cl.
CPC ............ *C12P 7/10* (2013.01); *C12P 19/02* (2013.01); *C12P 19/12* (2013.01); *C12P 19/14* (2013.01)

(58) Field of Classification Search
None
See application file for complete search history.

(56) References Cited

U.S. PATENT DOCUMENTS

2010/0330641 A1 12/2010 Nishimoto et al.

FOREIGN PATENT DOCUMENTS

| KR | 10-2013-0050399 A | 5/2013 |
|---|---|---|
| KR | 10-2014-0045764 A | 4/2014 |
| KR | 101497225 | 2/2015 |

OTHER PUBLICATIONS

Jagtap et al. (Saccharification of poplar biomass by using lignocellulases from Pholiota adiposa, Bioresource Technology, vol. 120, Sep. 2012, pp. 264-27, hereinafter Jagtap (2012).*
Jagtap et al. (Enzymatic hydrolysis of aspen biomass into fermentable sugars by using lignocellulases from Armillaria gemina, Bioresource Technology, vol. 133, Apr. 2013, pp. 307-314, herein after Jagtap et al. (2013).*
Dhiman "Simultaneous pretreatment and saccharification: Green technology for enhanced sugar yields from biomass using a fungal consortium" Bioresource Technology, 179, pp. 50-57, 2015.
Priyadharshini Ramachandran et al. "Saccharification of sunflower stalks with high metal content using lignocellulases from a fungal consortium comprising pholiota adipose and armillaria gemina", 11th International Phytotechnologies Conference 2014.

* cited by examiner

*Primary Examiner* — Iqbal H Chowdhury
(74) *Attorney, Agent, or Firm* — Baker & Hostetler LLP

(57) ABSTRACT

Provided are a method of preparing biofuel, in which the method includes obtaining saccharificated products from lignocelluosic biomass in high saccharification yield, and a simultaneous pretreatment and saccharification (SPS), in which the method includes a first step of pulverizing biomass and immersing the pulverized biomass; and a second step of preparing saccharificated products by performing the simultaneous pretreatment and saccharification of the immersed biomass with the enzyme produced by inoculating a fungal consortium in a culture medium and culturing the fungal consortium. In addition, the second step further includes a detoxification of decreasing or removing toxic materials through laccase produced by culturing with a strain producing laccase in the second step.

9 Claims, 17 Drawing Sheets

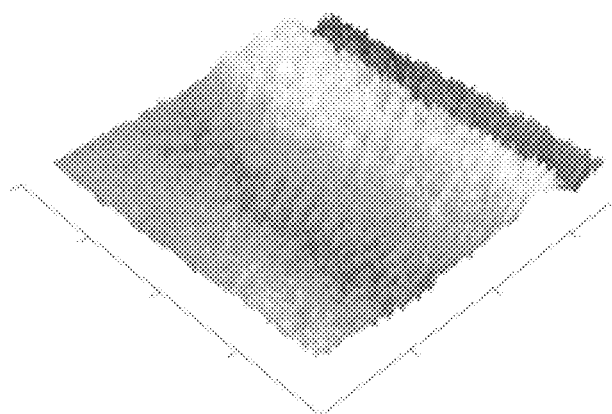
FIG. 11A.1
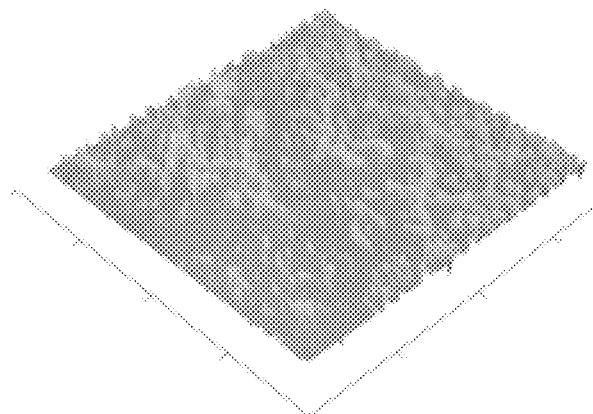
FIG. 11A.2
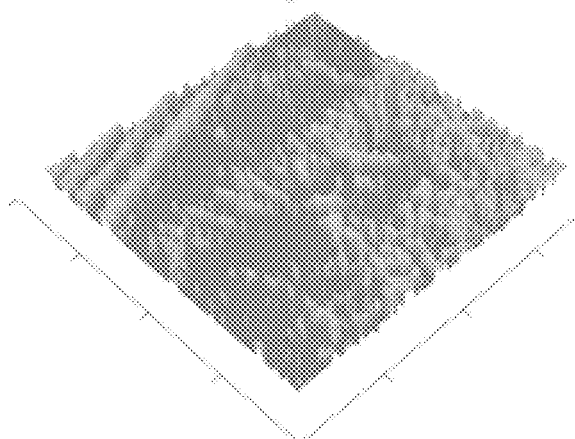
FIG. 11A.3

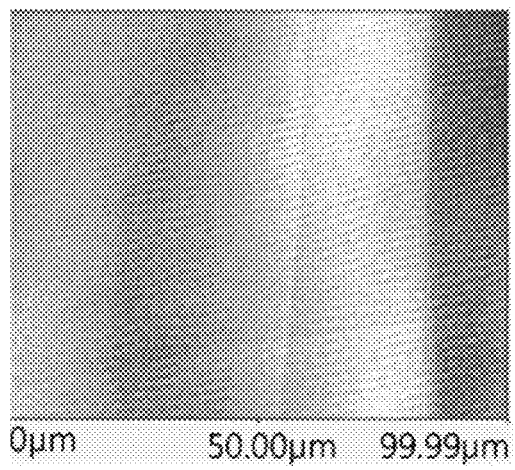
FIG. 11B.1
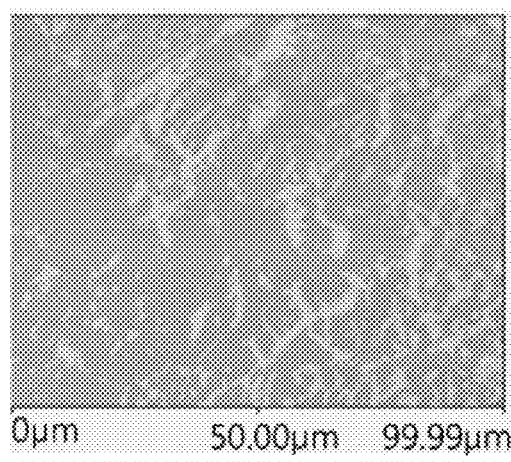
FIG. 11B.2
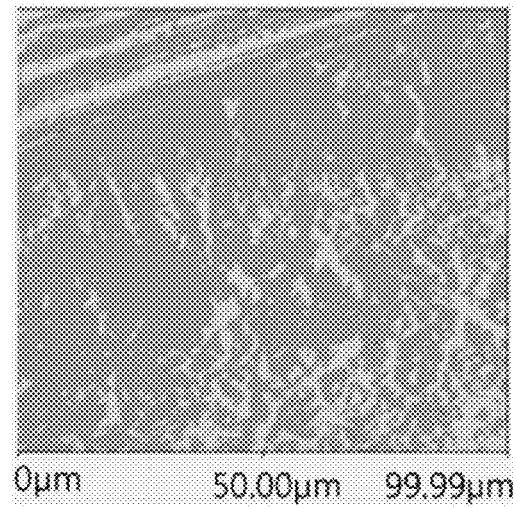
FIG. 11B.3

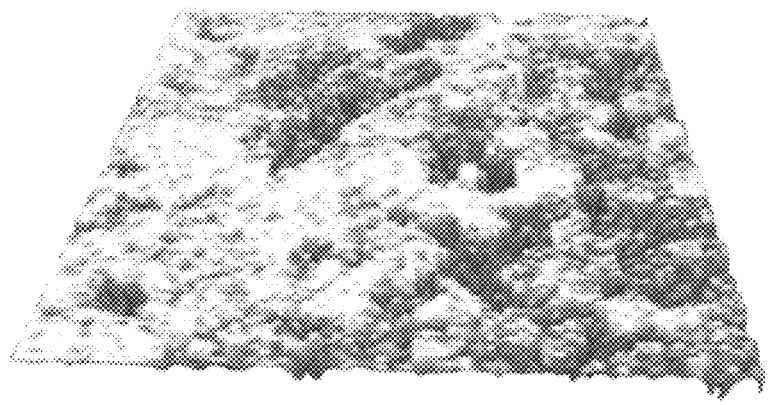
FIG. 11C.1
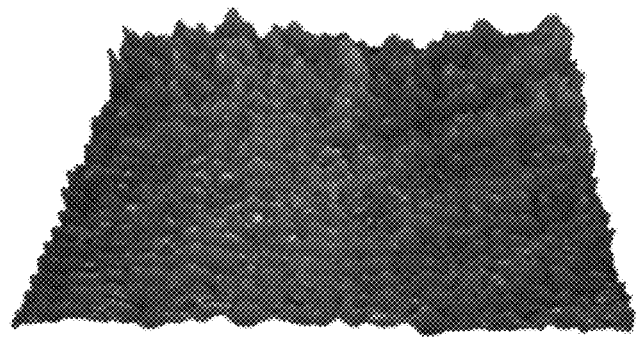
FIG. 11C.2
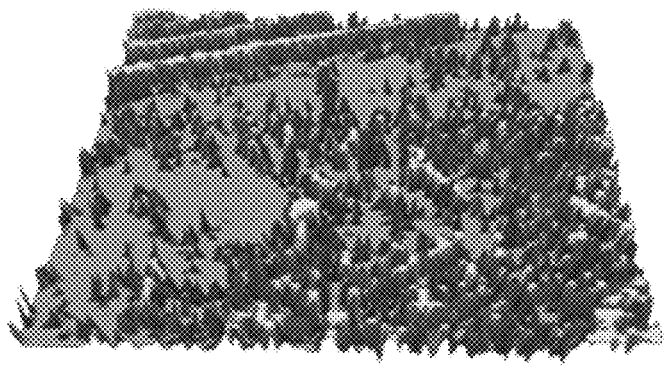
FIG. 11C.3

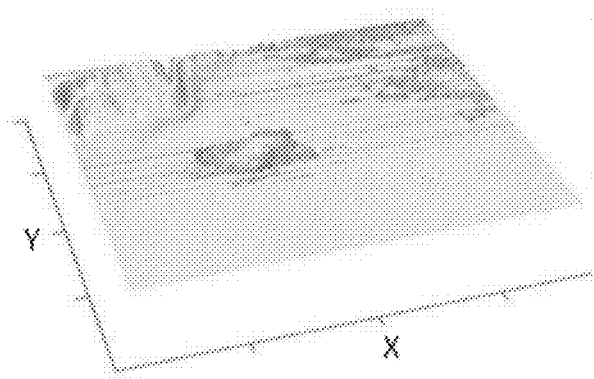
FIG. 12A.1
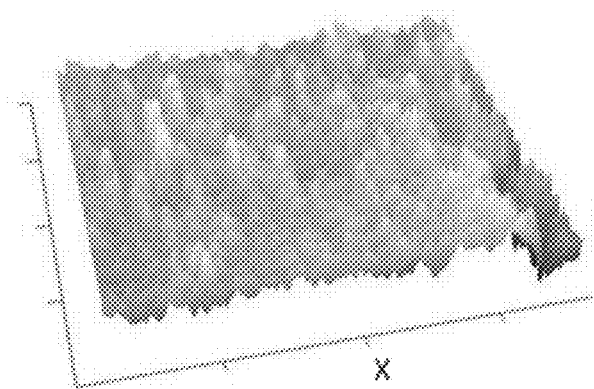
FIG. 12A.2
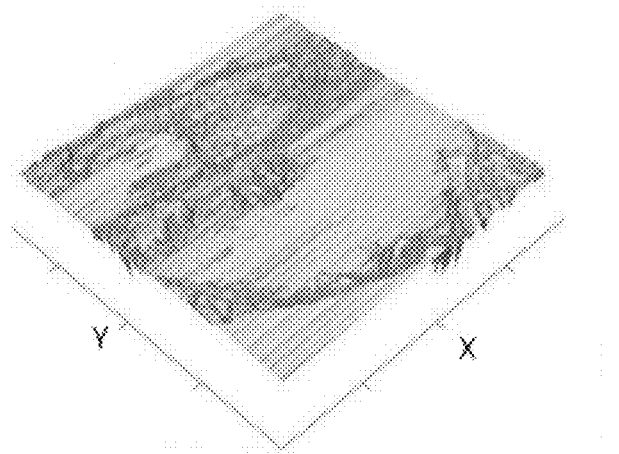
FIG. 12A.3

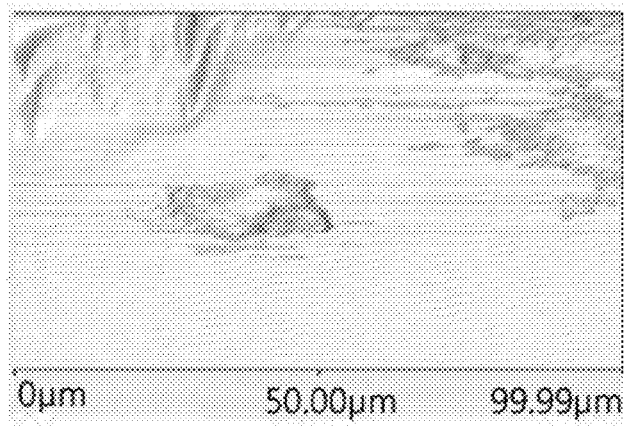
FIG. 12B.1
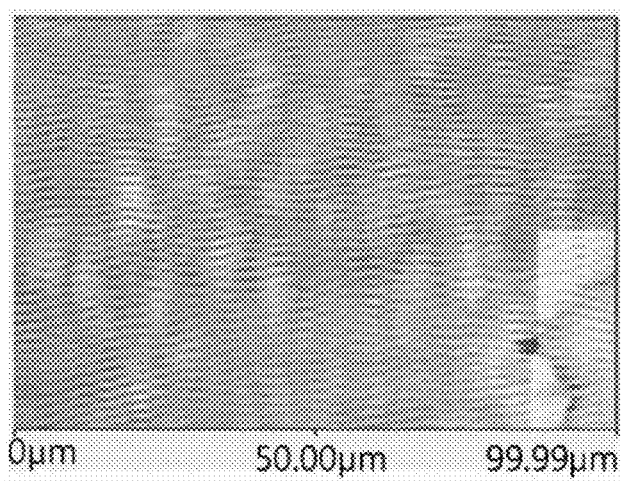
FIG. 12B.2
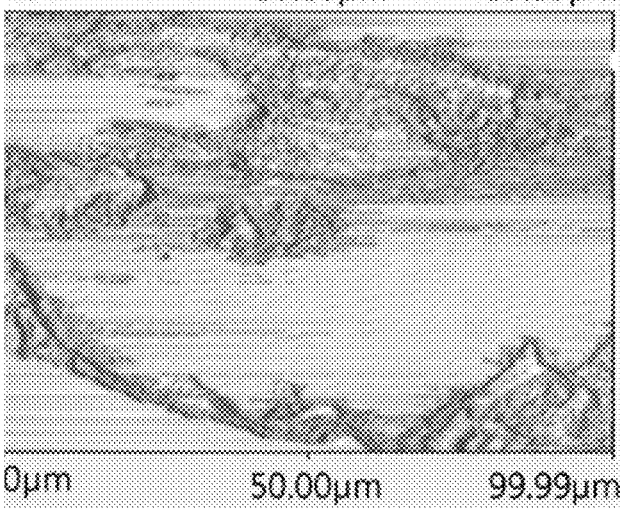
FIG. 12B.3

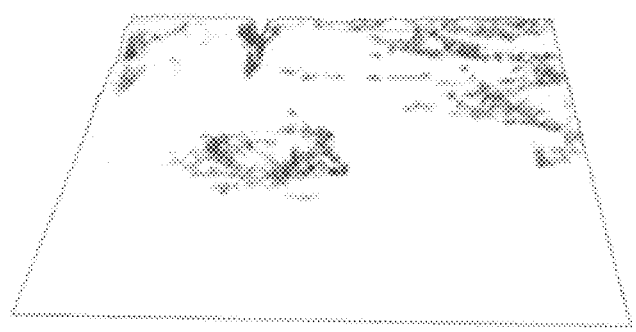
FIG. 12C.1
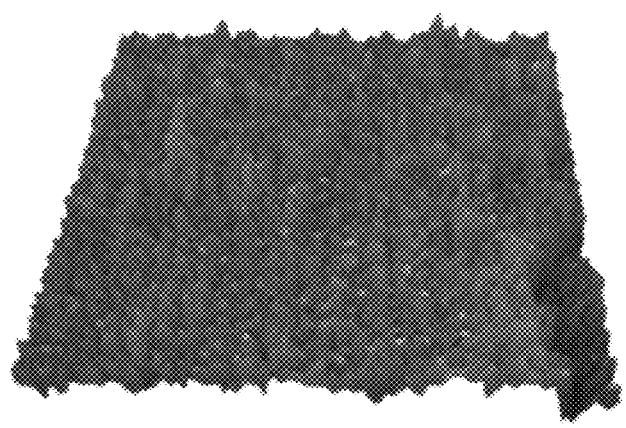
FIG. 12C.2
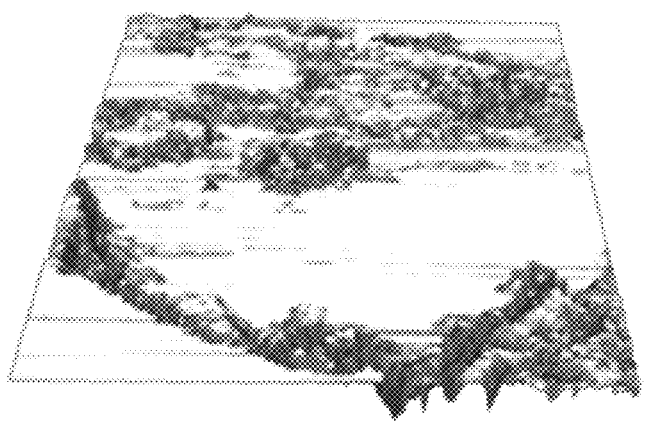
FIG. 12C.3

SIMULTANEOUS PRETREATMENT AND SACCHARIFICATION OF BIOMASS USING FUNGAL CONSORTIUM AND METHOD OF PREPARING BIOFUEL USING THE SAME

CROSS-REFERENCE TO RELATED APPLICATIONS

This application is based on and claims priority from Korean Patent Application No. 10-2015-0056209, filed on Apr. 21, 2015, with the Korean Intellectual Property Office, the disclosure of which is incorporated herein in its entirety by reference.

SEQUENCE LISTING

The instant application contains a sequence listing which has been submitted electronically in ASCII format and is hereby incorporated by reference in its entirety. Said ASCII copy, created on Jun. 15, 2015, is named 087248.003050 Sequence Listing and is 1 KB in size.

TECHNICAL FIELD

The present invention relates to a simultaneous pretreatment and saccharification of biomass using a fungal consortium, a method of preparing biofuel using the method, and a composition thereof.

BACKGROUND

There is a rising interest on producing new renewable energy, especially, energy using biomass, due to the depletion of fossil fuels and $CO_2$ saving effort all around the world. Among various biomass resources, lignocellulosic biomass has an advantage in that the shortfall in lignocellulosic biomass is the biggest and there are no ethical issues because lignocellulosic biomass is not irrelevant to the foodstuffs. Therefore, the production and development of the second-generation useful bio products using lignocelluloses that are lignocellulosic resources.

Lignocellulosic biomass is largely composed of lignin, cellulose, and hemicelluloses, which are carbohydrates.

It is known that lignin is a polymer having a large molecular weight including a large amount of aromatic compounds, in which methoxylated p-coumacyl alcohol, coniferylalcohol, synapyl alcohol, and the like are polymerized, and the decomposition of lignin is the most difficult among the natural compounds in the natural world. It is also known that cellulose is a polysaccharide prepared by binding glucoses with 1,4-linkage, and has a linear structure, so as to be in a stable type, thereby having physically and chemically strong structure. Hemicelluloses are a polysaccharide having low degree of polymerization of sugar as compared with cellulose, is mainly composed of xylan that is a polymer of xylose that is pentose, and furthermore, is composed of arabinose that is pentose, mannose, galactose, and glucose that are hexose.

The production of biomass using lignocellulosic biomass requires pretreatment, saccharification, and fermentation. Among them, the processes for improving the reaction rate and yield of enzymatic hydrolysis are commonly called the pretreatment. According to the pretreatment, the complex of lignin, cellulose, and hemicelluloses, which is a non-degradable aromatic polymer, is decomposed to reduce a degree of crystallization, increase the accessibility of enzyme, and increase the specific surface area of biomass, thereby increasing the amount of the effective enzyme. According to the degree of the pretreatment efficiency, the cost of preparing biomass is determined. Therefore, the pretreatment is one of the important factors for producing biomass.

As the pretreatment and saccharification for promoting the fermentability of lignocellulosic biomass, there is a method using a physical and chemical enzyme, which requires hydrolysis for obtaining the monosaccharide of pentose or hexose as a useful fermentable saccharificated product capable of being used by microorganisms from biomass materials. According to the method, lignin is typically penetrated by increasing the content of cellulose and decreasing the crystallinity of microfilament, and the reactivity and hydrolysis ability of hemicelluloses are increased by increasing the accessibility and the adsorption rate of cellulose hydrolase per unit area.

As a physically pretreatment, there are a ball milling, an ultrasonic milling, homogenization, and the like. According to the physically pretreatment, the particle size of biomass material is decreased to increase a specific surface area, and decrease the degree of polymerization of cellulose. However, the energy consumption thereof is high, and thus, the physical pretreatment is not favorable.

In addition, a chemical pretreatment is a hydrolysis using an acid and base, and is usually used in the pretreatment of biomass. However, according to the chemical pretreatment, the monosaccharides are not only produced, but toxic materials, for example, furfural, vanillin, weak acids, such as, ferulic acid and coumaric acid, furan derivatives, and phenolic compounds, that may seriously affect the growth of microorganism, may be induced so as to greatly affect on reducing the efficiency of the following fermentation. Therefore, a detoxification process is required to remove inhibitors from the substrate as the previous process before the fermentation.

PATENT DOCUMENTS

Korean Patent No. 10-1497225

SUMMARY

As described above, a general pretreatment and saccharification further requires a washing process for removing toxic materials. The washing process uses a great quantity of water, and thus, the environment pollution and energy consumption occur. In addition, there are many cases of washing biomass used as a raw material during the washing process, and thus, the energy efficiency rate is decreased. Therefore, it is being required to develop the effective and eco-friendly pretreatment and saccharification for lignocellulosic biomass.

In order to solve the above-described problems, a main object of the present invention is to provide a simultaneous pretreatment and saccharification method of biomass for decreasing the loss of biomass and improving the yield of saccharification.

Another object of the present invention is to provide a method of preparing biomass, which can effectively, economically, and eco-friendly provide biomass by fermenting saccharificated products obtained from biomass with fermentation strains through the simultaneous pretreatment and saccharification method.

Still another object of the present invention is to provide a composition for the simultaneous pretreatment and saccharification, which includes a fungal consortium capable of obtaining saccharificated products from biomass in the simultaneous pretreatment and saccharification method as an effective component.

Still another object of the present invention is to provide a composition for preparing biomass, which includes a fermentation strain for fermenting saccharificated products obtained from biomass in the method of preparing biomass as an effective component.

In order to obtain the above-described objects, the simultaneous pretreatment and saccharification method of biomass includes a first step of pulverizing biomass and immersing the pulverized biomass and a second step of preparing saccharificated products by performing the simultaneous pretreatment and saccharification of the immersed biomass with the enzyme produced by inoculating a fungal consortium in a culture medium and culturing the fungal consortium.

The second step may further include a detoxification process for reducing or removing toxic materials through laccase produced by culturing a strain producing laccase, in which the strain producing laccase is *Tyromyces chioneus*.

In addition, the second step may further include a surfactant, in which the surfactant may be any one selected from the group consisting of polyoxyethylene sorbitan monolaurate (Tween-20) and polyoxyethylene sorbitan monooleate (Tween-80).

The fungal consortium may include *Pholiota adipose* and *Armillaria gemina*, in which the *Pholiota adipose* and *Armillaria gemina* are mixed in a weight ratio of 1:2, and then, the amount of two strains may be inoculated in 10% (v/v) or less in a culture medium.

The fungal consortium is cultured in the culturing conditions of the culture time of 36 to 48 hours, the culture temperature of 20 to 30° C., the pH of culture medium of 4 to 6.5, and the stirring rate of 50 to 300 RPM.

The enzyme may be any one selected from the group consisting of cellulase, xylanase, endoglucanase (EG), β-glucosidase (BGL), and cellobiohydrolase (CBH).

The method of preparing biomass of the present invention includes fermenting saccharificated products prepared by the simultaneous pretreatment and saccharification of biomass as described above, in which according to the fermentation, provided is a method of preparing biomass including inoculating a fermentation strain into the saccharificated products, culturing the strain, and then, fermenting the products.

The fermentation strain is *Saccharomyces cerevisiae*, and is cultured in the culturing conditions of the culture time of 48 hours, the culture temperature of 35° C., the pH of the culture medium of 5, and the stirring rate of 90 to 110 RPM.

The composition for the simultaneous pretreatment and saccharification of the present invention may include *Pholiota adipose* and *Armillaria gemina* as a fungal consortium in a culture medium for preparing saccharificated products from biomass, in which *Tyromyces chioneus* may be further included as a strain for producing laccase, and also, a surfactant may be further included.

The surfactant is any one selected from the group consisting of polyoxyethylene sorbitan monolaurate (Tween-20) and polyoxyethylene sorbitan monooleate (Tween-80).

In addition, the *Pholiota adipose* and *Armillaria gemina* are mixed in the ratio of 1:2, and the amounts of two strains in the culture medium are included in 10% (v/v) or less.

The composition for preparing biofuel of the present invention includes *Saccharomyces cerevisiae* as a yeast for fermenting saccharificated products produced from biomass, and the *Saccharomyces cerevisiae* is included in the amount of 2% (v/v) in the culture medium.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 11A.1, FIG. 11A.2, and FIG. 11A.3 represent the 3-D surface analysis result of measuring rice straw with an atomic force microscopy (AFM) according to an embodiment of the present invention.

FIG. 11B.1, FIG. 11B.2, and FIG. 11B.3 represent the average surface roughness (ASR) result of measuring rice straw with an atomic force microscopy (AFM) according to an embodiment of the present invention.

FIG. 11C.1, FIG. 11C.2, and FIG. 11C.3 represent the dark field surface analysis result of measuring rice straw with an atomic force microscopy (AFM) according to an embodiment of the present invention.

FIG. 12A.1. FIG. 12A.2, and FIG. 12A.3 represent the 3-D surface analysis result of measuring willow with an atomic force microscopy (AFM) according to an embodiment of the present invention.

FIG. 12B.1, FIG. 12B.2, and FIG. 12B.3 represent the average surface roughness (ASR) result of measuring willow with an atomic force microscopy (AFM) according to an embodiment of the present invention.

FIG. 12C.1, FIG. 12C.2 and FIG. 12C.3 represent the dark field surface analysis result of measuring willow with an atomic force microscopy (AFM) according to an embodiment of the present invention.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present invention will be described with reference to the following Examples in more detail, but the present invention is not limited to Examples.

Figure 1:
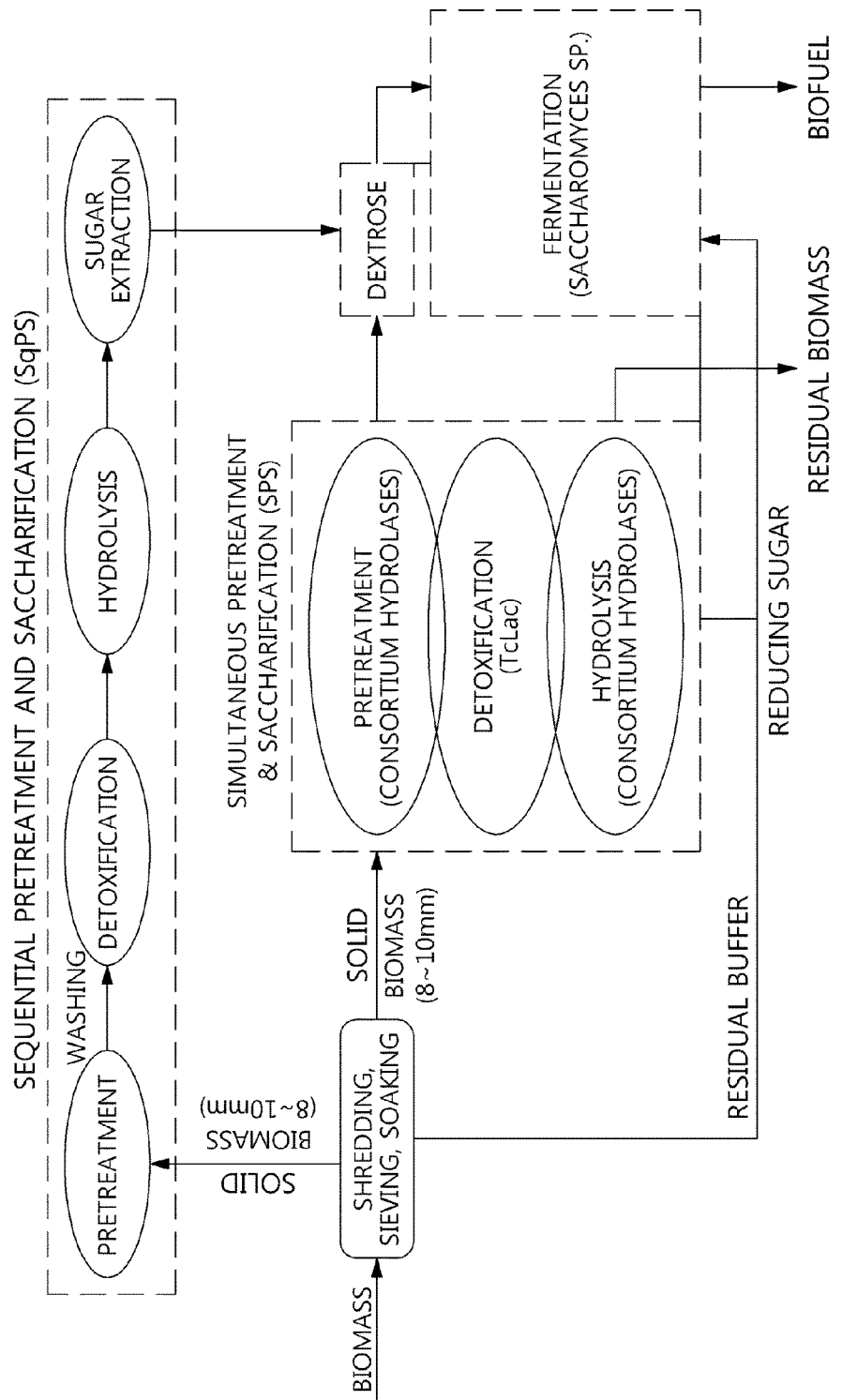
FIG. 1 is a flow chart of the simultaneous pretreatment and saccharification method and the method of preparing biofuel according to the present invention.

The present invention relates to a simultaneous pretreatment and saccharification of biomass, which can reduce the generation of toxic by-product and the loss of biomass and can improve the saccharification yield. As illustrated in FIG. 1, the method includes a first step of pulverizing biomass and immersing the pulverized biomass, and a second step of performing a simultaneous pretreatment and saccharification of the immersed biomass using the enzyme produced by culturing a fungal consortium in a culture medium. The biomass that is pretreated or saccharificated in the second step includes a toxic material, and thus, the method further includes a detoxification process of reducing or removing the toxic material by laccase.

The biomass is derived from a plant, and preferably, is lignocellulosic biomass, and may include willow and rice straw. However, the present invention is not limited thereto. In Examples of the present invention, willow and rice straw are used as a biomass material. *Salix koreensis* is used as willow and *Oryza sativa* L. is used as rice straw.

In the first step according to Example of the present invention, the pulverizing is performed using a hammer mill in the case of willow (*Salix koreensis*); the willow chip pulverized to have the size of about 8 to 10 mm is subjected to a disk milling to separate the chips having the size of 15 mm or more and less than 6 mm; and finally, the chips are pulverized be the thickness of about 2 to 6 mm. *Oryza sativa* L. is cut to be in the length of about 5 cm and then is ground to be the size of about 4 mm.

In addition, the ground solid biomass is mixed with a buffer solution in the ratio of 1:15 (w/v), and then, immersed for a physical treatment of the solid biomass. At this time, the buffer is 0.1 mole concentration (M) of sodium acetate buffer, and the sodium acetate buffer of pH 5 may be preferably used in order to optimize the enzyme produced from a fungal consortium.

In the second step according to Example of the present invention, the simultaneous pretreatment and saccharification (SPS) uses a fungal consortium, biologically.

For the production of high activity enzyme that degrade lignin and lignocelluloses that is a complex matrix of lignocellulosic biomass in the present invention, a simultaneous pretreatment and saccharification may be performed using complex strains as a fungal consortium to produce saccharificated products.

Meanwhile, the experimental method of the strain identification of strains for the fungal consortium is as follows.

In order to isolate strains producing an enzyme, the strain was smeared on a solid agar plate including 2% carboxymethylcellulose (CMC), and then, cultured for 3 days. The colony of strains that was formed on the solid agar plate was stained with 0.1% Congo Red reagent and was decolorized with 0.1 M sodium chloride to isolate the strains producing an enzyme using a red agar plate method for selecting the strains producing a cellulose decomposing circle around the colony.

In order to identify the isolated strains, the strain was identified with an base sequence analyzing method using internal transcribed spacer of ribosomal DNA (ITS rDNA). For ITS1-5.8S-ITS2 rDNA of the strain, the gene having 780 bp and 592 bp amplicons was amplified by performing PCR (polymerase chain reaction) with the primers of SEQ ID NOs:1 and 2.

<SEQ ID NO:1>
pITS1 5'-TCCGTAGGTGAACCTGCCG-3'
<SEQ ID NO:2>
pITS4 5'-TCCTCCGCTTATTGAT-ATGC-3'

In addition, for species relationship analysis, the phylogenetic tree of the base sequences was prepared using DNAstar and MegAlign software (Madison, Wis., USA), and the species inherited relationship might be compared.

Figure 2:
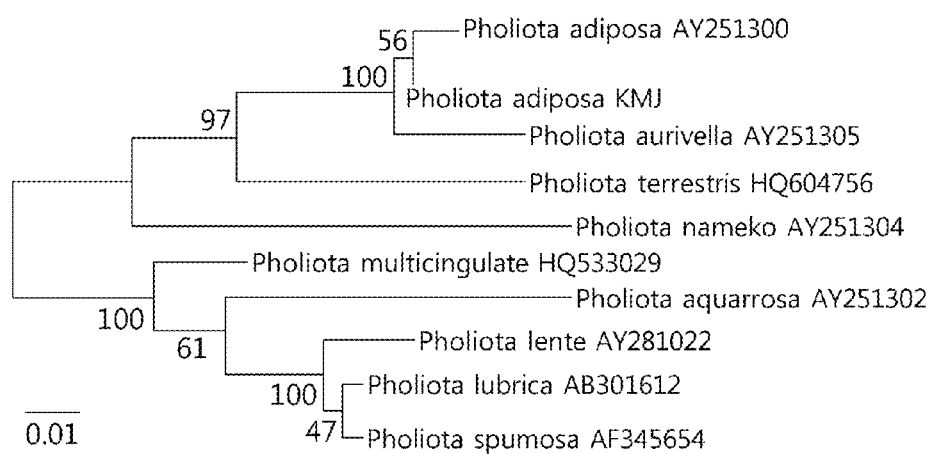
FIG. 2 is a schematic diagram of phylogenetic dendrogram for *Pholiota adipose* in a fungal consortium of the present invention.
Figure 3:
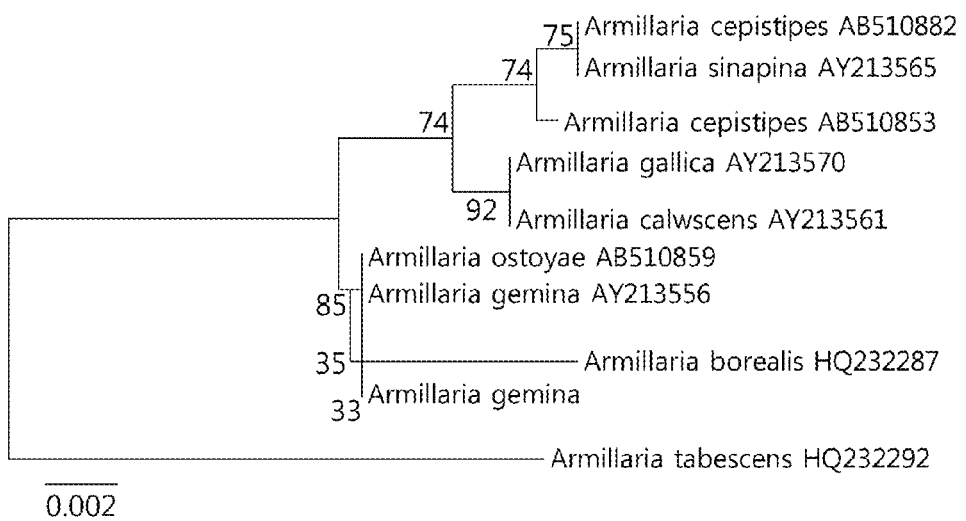
FIG. 3 is a schematic diagram of phylogenetic dendrogram for *Armillaria gemina* in a fungal consortium of the present invention.

The relationship of the base sequence of ITS1-5.8S-ITS2 rDNA of the selected strain with similar specie was searched with BLAST to analyze the identification and analysis of each of the fungal. As a result, the strains were JF719544 and JF7825075 that were accession numbers of GenBank. As illustrated in FIGS. 2 and 3, the strains were *Pholiota adipos* and *Armillaria gemina* strains that were classification situations, and also, it could be confirmed that the accession numbers were 11187P and 11186P, respectively at Korean Culture Center of Microorganisms (KCCM).

Figure 4:
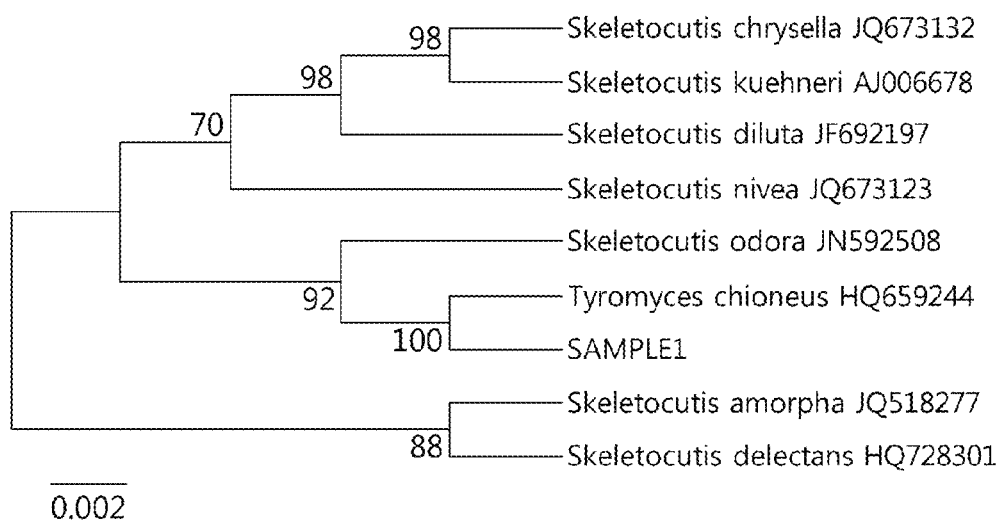
FIG. 4 is a schematic diagram of phylogenetic dendrogram for *Tyromyces chioneus* that is a strain of producing lacasse of the present invention.

In addition, with the above-described method, the stain that produces laccase was cultured on the solid agar medium including 0.2% ABTS (2,2'-azino-bis(3-ethylbenzothiazoline-6-sulphonic acid)) and isolated. The base sequence of ITS1-5.8S-ITS2 rDNA was amplified and analyzed with the above-described strain identification method. As a result, it could be confirmed that the stain exhibited the highest similarity with *Tyromyces chioneus* strain (KCCM accession number: KFCC11873P) as illustrated in FIG. 4.

The enzyme that was produced from *Pholiota adipose* and *Armillaria gemina*, the fungal consortium of complex other strains may include any one selected from the group consisting of cellulase, xylanase, endoglucanase (EG), β-glucosidase (BGL), and amdcellobiohydrolase (CBH).

For the measuring of the activity of complex enzyme produced from the fungal consortium, the activities of the above-described enzymes may be measured using a DNS (dinitroxalicylic acid) method using carboxymethylcellulose (CMC), p-nitrophenyl glucoside (pNPG), and p-nitrophenyl cellobioside (pNPC) as a substrate. Here, 1 unit that was a unit of enzyme activity may be defined as the amount of enzyme producing 1 μmol of reducing sugar per a minute in 1 mL.

As listed in Tables 1 and 2, for the optimum culturing conditions for producing enzyme, it could be confirmed that the activity of enzyme depended on various kinds of carbon sources and nitrogen sources in a culture medium. Here, as the culturing conditions, two strains, such as, *Pholiota adipose* and *Armillaria gemina* in the ratio of 1:1 were cultured at the temperature of 25° C., pH 5.0, and 100 RPM for 10 days.

As a result, it could be confirmed from Table 1 that in the case of using cellulose and Avicel as a carbon source, the production of enzyme was high. In general, the proper activity of enzyme was 0.6 FPU/mL to 0.8 FPU/mL. Here, what bran was the residue remained after producing grains;

thus, was economical in term of cost; and thus, might be used as a carbon source for producing proper enzyme.

In addition, it could be confirmed from the result showing the activity degree of enzyme depending on the nitrogen sources as listed in Table 2 that peptone was used as a nitrogen source for producing proper enzyme.

TABLE 1

| Carbon sources | FPU (U/mL) | Protein amount (mg/mL) | pH |
| --- | --- | --- | --- |
| Glucose | 0.63 | 0.82 | 4.89 |
| Maltose | 0.42 | 0.84 | 4.72 |
| Sucrose | 0.44 | 0.86 | 4.89 |
| Cellulose | 0.98 | 0.98 | 4.92 |
| Carboxy methylcellulose | 0.84 | 0.91 | 4.93 |
| Avicel | 0.76 | 0.96 | 4.84 |
| Rice straw | 0.54 | 0.79 | 4.89 |
| Wheat bran | 0.68 | 0.86 | 4.89 |

TABLE 2

| Nitrogen sources | FPU (U/mL) | Protein amount (mg/mL) | pH |
| --- | --- | --- | --- |
| Yeast extract (YE) | 0.54 | 0.79 | 4.82 |
| Peptone (P) | 0.87 | 0.96 | 4.79 |
| Corn steep solid (CSS) | 0.54 | 0.68 | 4.86 |
| YE + P | 0.76 | 0.72 | 4.89 |
| YE + CSS | 0.52 | 0.79 | 4.72 |
| KNO$_3$ | 0.41 | 0.66 | 4.56 |
| NH$_4$Cl | 0.43 | 0.66 | 4.83 |

In addition, the affect of the strain on the activity of enzyme, lignocellulase, depending on the ratio of each of the strains was confirmed in the fungal consortium. Here, the medium included the composition including wheat bran (20 g/L), peptone (15 g/L), yeast extract (9 g/L), KH$_2$PO$_4$ (15 g/L), K$_2$HPO$_4$ (15 g/L), MgSO$_4$ (3 g/L), KNO3 (1 g/L), inositol (0.02 g/L), and thiamine hydrochloride pentahydrate (0.02 g/L).

As a result, it could be confirmed from Table 3 that the optimist mixing ratio of strains in the mixing ratio of two types from the fungal consortium was 1:2 of *Pholiota adipose* and *Armillaria gemina*, and in this case, the highest enzyme activity was shown. At this time, the total amount of inoculated materials to two strains in the medium volume should be 10% (v/v) or less.

TABLE 3

| Pholiota adiposa | Armillaria gemina | FPU (U/mL) |
| --- | --- | --- |
| 1 | 1 | 0.71 ± 0.08 |
| 1 | 2 | 0.86 ± 0.09 |
| 1 | 3 | 0.78 ± 0.09 |
| 2 | 1 | 0.64 ± 0.08 |
| 2 | 3 | 0.79 ± 0.07 |
| 3 | 1 | 0.72 ± 0.08 |
| 3 | 2 | 0.68 ± 0.07 |

As the condition of enzyme activity of the fungal consortium of the present invention, the optimum enzyme activities depending on the affects of the temperature, pH, and RPM (rotation per minutes) were tested.

The two stains, *Pholiota adipose* and *Armillaria gemina* of the fungal consortium were mixed in the ratio of 1:2, and were cultured in the pH 5 medium including wheat bran as a carbon source at 100 RPM for 10 days. The results of the enzyme activity depending on the culturing temperature of fungal consortium are listed in the following Table 4. As a result, it could be confirmed that the optimum temperature of the enzyme activity was 22.5° C.

TABLE 4

| Temperature (° C.) | FPU (U/mL) | Protein (mg/mL) |
| --- | --- | --- |
| 20 | 0.88 ± 0.09 | 1.02 ± 0.08 |
| 22.5 | 1.11 ± 0.12 | 1.22 ± 0.15 |
| 25 | 0.94 ± 0.08 | 1.15 ± 0.11 |
| 27.5 | 0.72 ± 0.08 | 0.85 ± 0.10 |
| 30 | 0.58 ± 0.06 | 0.72 ± 0.08 |

Figure 5:
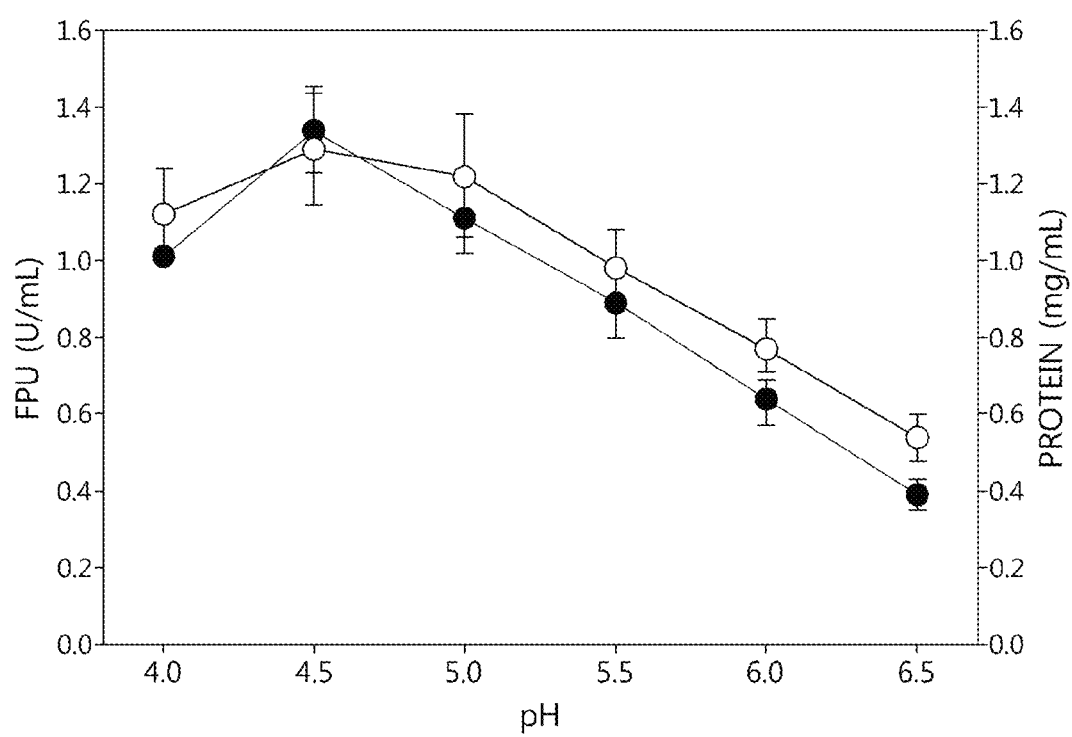
FIG. 5 is the result of measuring the productions of enzyme in relation to the concentrations of pH as an embodiment of the present invention.
Figure 6:
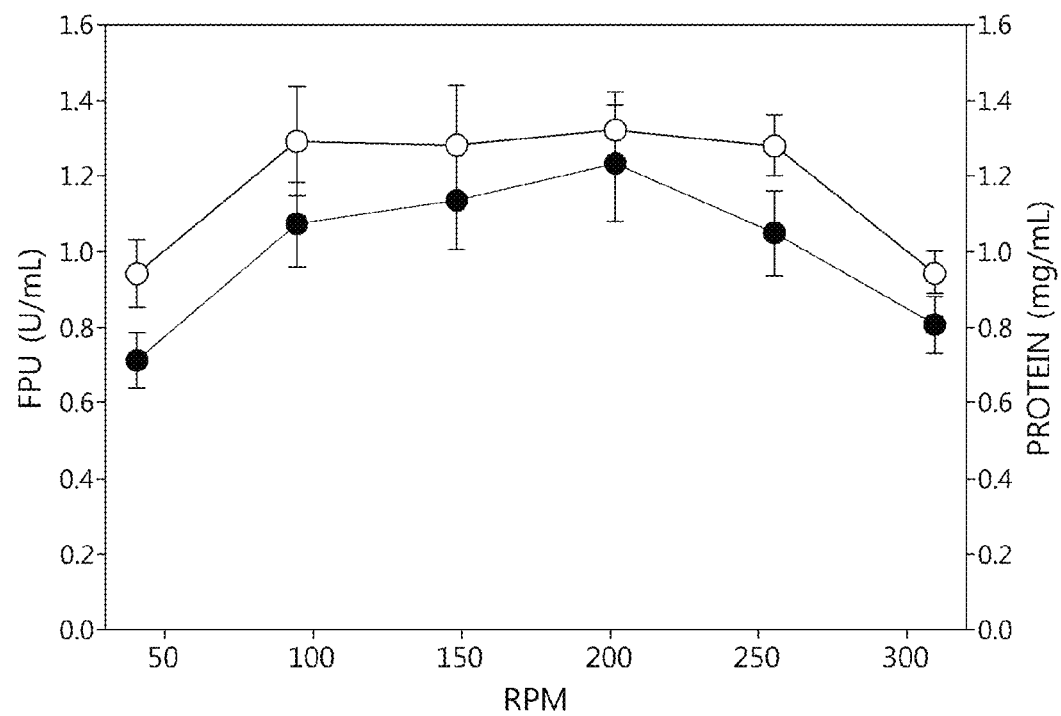
FIG. 6 is the result of measuring the productions of enzyme in relation to the RPM rates as an embodiment of the present invention.

FIGS. 5 and 6 are the results of measuring the optimum pH concentration and optimum RPM rate of the enzyme activities, respectively. In the illustrated graph, "○" represents an enzyme activity (FPU/mL) and "●" represents a protein amount (mg/ml).

As illustrated in FIG. 5, two strains, *Pholiota adipose* and *Armillaria gemina* of the fungal consortium were mixed in the ratio of 1:2, and were cultured in the medium with wheat bran as a carbon source at the temperature of 22.5±0.5° C. and the rate of 100 RPM for 10 days. As the optimum conditions of enzyme activity depending on the change of pH concentrations, the enzyme activity was measured at pH 4.0 to pH 6.5. As a result, it could be confirmed that the enzyme activity was highest at pH 4.5.

In addition, FIG. 6 illustrates the results of measuring the optimum RPM rate for producing enzyme. Two strains, *Pholiota adipose* and *Armillaria gemina* of the fungal consortium were mixed in the ratio of 1:2, and were cultured in the medium with wheat bran as a carbon source at the temperature of 22.5±0.5° C. and pH 4.5 for 10 days. It could be confirmed that the enzyme activity was highest at 200 RPM from the range of 50 RPM to 300 RPM.

Therefore, as a result of testing the conditions of enzyme activity in the fungal consortium, it could be confirmed that the enzyme exhibited high enzyme activity, 2.57 U/ml when the optimum temperature of enzyme activity was 22.5° C., pH was 4.5, the stirring rate was 200 RPM, peptone was used as a nitrogen source, and wheat bran was used as a carbon source.

In addition, for the activity of each of enzymes produced from the fungal consortium in the above-described optimum enzyme activity conditions, it could be confirmed that xylanase exhibited 1870±252 U/mL, endoglucanase (EG) exhibited 176±23 U/mL, cellobiohydrolase (CBH) exhibited 44±5 U/mL, and β-glucosidase (BGL) exhibited 39±5 U/mL, the FPU (filter paper activity unit) of 2.57±0.5.

The saccharification that hydrolyzes biomass was a previous step of the fermentation process for producing biofuel from a biomass material, and the process of converting cellulose into a disaccharide and a monosaccharide, such as, glucose capable of being fermented with ethanol.

As a method for measuring the activity of saccharification in the simultaneous pretreatment and saccharification according to Example, the enzyme produced in the fungal consortium after the saccharification was subjected to a heat shock at 90° C. or less for 1 minute to modify and cool the enzyme, and then, centrifuged at 4000 rpm for 30 minutes to obtain the saccharificated products, that were reducing sugar isolated in the supernatant. The yield of saccharification was measured from the saccharification product.

In the saccharification according to Example of the present invention, the change of saccharification yields by a substrate and enzyme amount was measured by performing the saccharification while mixing at the temperature of 30°

C., pH 5, and 90 to 110 RPM for 36 hours. The results thus obtained are listed in the following Table 5.

TABLE 5

| Enzyme amount (FPU/g substrate) | Type of substrate | Reducing sugar (mg/g-substrate) | Saccharification yield (%) |
|---|---|---|---|
| 5 | RS | 212 ± 19 | 42.4 ± 3.2 |
| 5 | W | 65.0 ± 7.4 | 13.9 ± 1.5 |
| 7.5 | RS | 276 ± 22 | 55.2 ± 4.2 |
| 7.5 | W | 119 ± 12 | 25.5 ± 3.1 |
| 10 | RS | 313 ± 24 | 62.6 ± 6.6 |
| 10 | W | 158 ± 17 | 33.8 ± 3.3 |
| 12.5 | RS | 315 ± 29 | 63.1 ± 6.2 |
| 12.5 | W | 191 ± 19 | 40.9 ± 4.3 |
| 15 | W | 251 ± 23 | 53.7 ± 5.2 |
| 20 | W | 254 ± 24 | 54.4 ± 4.9 |
| 10 | Raw RS | 64.2 ± 5.3 | 12.8 ± 2.1 |
| 15 | Raw W | 66.4 ± 6.1 | 14.1 ± 2.2 |
| 10 | Alkali pretreated RS | 377 ± 25 | 75.4 ± 7.1 |
| 15 | Alkali pretreated W | 301 ± 23 | 64.5 ± 6.6 |

In Table 5, as a type of substrate, RS represents immersed rice straw, W represents immersed willow, Raw RS represents untreated rice straw, Raw W represents untreated willow, pretreated RS represented pretreated rice straw, pretreated W represents pretreated willow, alkali pretreated RS represents the rice straw that was subjected to an alkali-mediated sequential pretreated and saccharification (SqPS), and alkali pretreated W represents the willow that was subjected to an alkali-mediated sequential pretreated and saccharification (SqPS).

As listed in Table 5, as a result of confirming the concentration of enzyme in the fungal consortium in the simultaneous pretreatment and saccharification (SPS) of the present invention in the range of 5 to 20 FPU/g substrate, it could be confirmed that the saccharification yield (%) was high in the concentration of 10 FPU/g substrate, but the saccharification yield (%) was low in the low concentration of 5 and 7.5 FPU and 15 FPU/g substrate or more.

Figure 7:
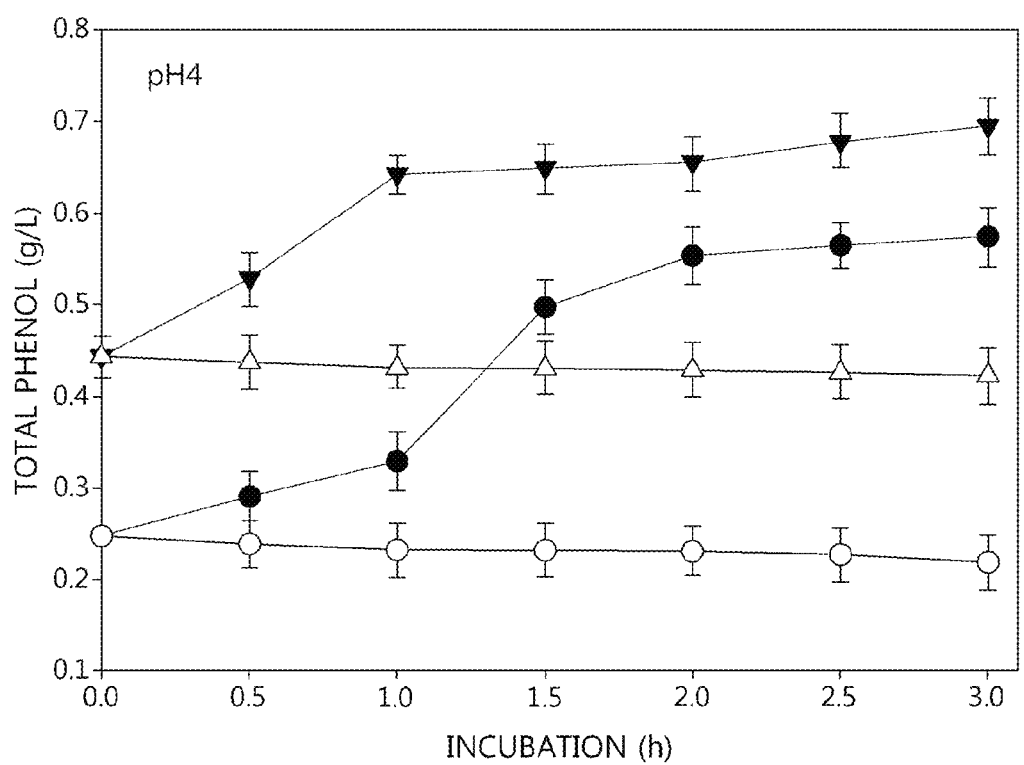
FIG. 7 is the result of measuring the change amounts of phenol contents by pH (pH 4) in an embodiment of the present invention.

FIGS. 6 and 7 illustrate the change of saccharification yield (%) depending on the culturing time and culturing temperature in the saccharification. In the Table, RS represents rice straw and W represents willow as biomass (substrate).

The following Table 6 shows the saccharification yields depending on the culturing time. It could be confirmed that in the cases of the culturing times, 36 hours and 48 hours, in the substrates, high saccharification yields were exhibited.

TABLE 6

| Culturing time (hour) | Type of substrate | Reducing sugar (mg/g-substrate) | Saccharification yield (%) |
|---|---|---|---|
| 12 | RS | 176 ± 16 | 35.2 ± 3.6 |
| 12 | W | 109 ± 6 | 23.3 ± 2.6 |
| 24 | RS | 245 ± 14 | 49.1 ± 5.1 |
| 24 | W | 176 ± 13 | 37.7 ± 4.1 |
| 36 | RS | 313 ± 24 | 62.6 ± 5.9 |
| 36 | W | 251 ± 23 | 53.7 ± 5.1 |
| 48 | RS | 315 ± 25 | 63.1 ± 6.4 |
| 48 | W | 255 ± 21 | 54.6 ± 5.5 |

The following Table 7 shows the changes of saccharification yields depending on the temperatures. As a result of culturing the enzyme concentration of 20 FPU/g-substrate and 30 FPU/g-substrate, pH of 5.0, and the rate of 100±10 RPM for 36 hours, it could be confirmed that the saccharification yield (%) was highest at the temperature of 35° C., in which for different two substrates, the amount of reducing sugar produced in rice straw (RW) was 337±30 mg/g-substrate and the saccharification yield thereof was 67.4±6.6% and the amount of reducing sugar produced in willow (W), other substrate, was 270±22 mg/g-substrate and the saccharification yield thereof was 57.1±5.3%.

TABLE 7

| Temperature (° C.) | Type of substrate | Reducing sugar (mg/g-substrate) | Saccharification yield (%) |
|---|---|---|---|
| 25 | RS | 242 ± 22 | 48.4 ± 5.2 |
| 25 | W | 174 ± 15 | 37.2 ± 3.9 |
| 30 | RS | 313 ± 23 | 62.6 ± 6.6 |
| 30 | W | 251 ± 23 | 53.7 ± 5.2 |
| 35 | RS | 337 ± 30 | 67.4 ± 6.6 |
| 35 | W | 270 ± 22 | 57.1 ± 5.3 |
| 40 | RS | 285 ± 24 | 57.6 ± 5.4 |
| 40 | W | 229 ± 20 | 49.1 ± 4.5 |

The toxic materials that are generally known in the degradation products of lignocelluloses are largely classified into two classes, a phenolic compound and a non-phenolic compound. The phenolic compound is ferulic acid, coumaric acid, hydroxybenzoic acid, syringaldehyde, vanillin, and the like, that are mostly hydrolytic products of lignin.

The detoxification according to the present invention was the reaction for reducing or removing the toxic materials of the above-described phenolic compound produced in the simultaneous pretreatment and saccharification with a biological method. As an example, *Tyromyces chioneus*, which was a strain producing laccase, was inoculated in a medium, and was cultured while being stirred at 30° C. and the rate of 150 RPM (revolution per minute) for 4 hours. Laccase produced in TcLac ("TcLac" represents a strain producing lacase) was allowed to be included in 10 U/mL in the biomass prepared by immersing 1 g of dried weight of biomass in 25 mL of 50 mM buffer, so as to be detoxificated.

In general, laccase has low specificity to a substrate, and thus, is allowed to oxidize the phenolic compound that is widely distributed in the natural world, such as, polyphenol, methoxy-substituted phenol, and diamine. In addition, it is known that laccase that is produced in a fungus is involved in the degradation of lignin.

Therefore, TcLac may be used for the detoxification for oxidizing and removing phenolic compounds derived from biomass through the production of laccase, and also, for the pretreatment of the biomass. In addition, the TcLac of the present invention may be added with a fungal consortium.

Figure 8:
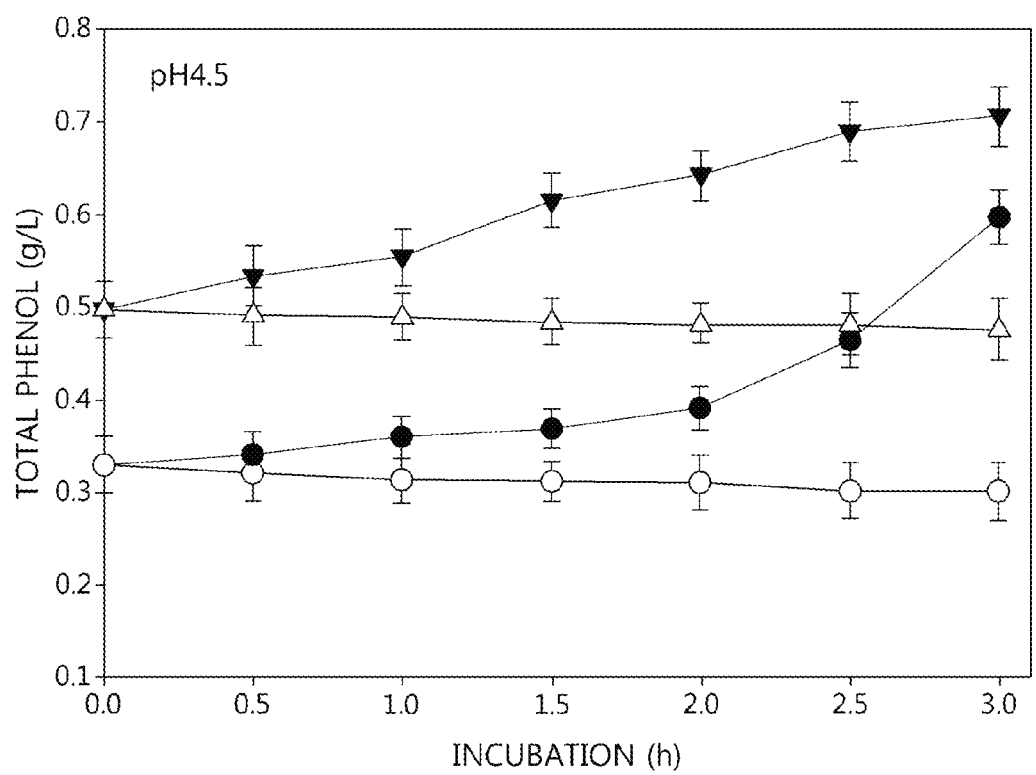
FIG. 8 is the result of measuring the change amounts of phenol contents by pH (pH 4.5) in an embodiment of the present invention.
Figure 9:
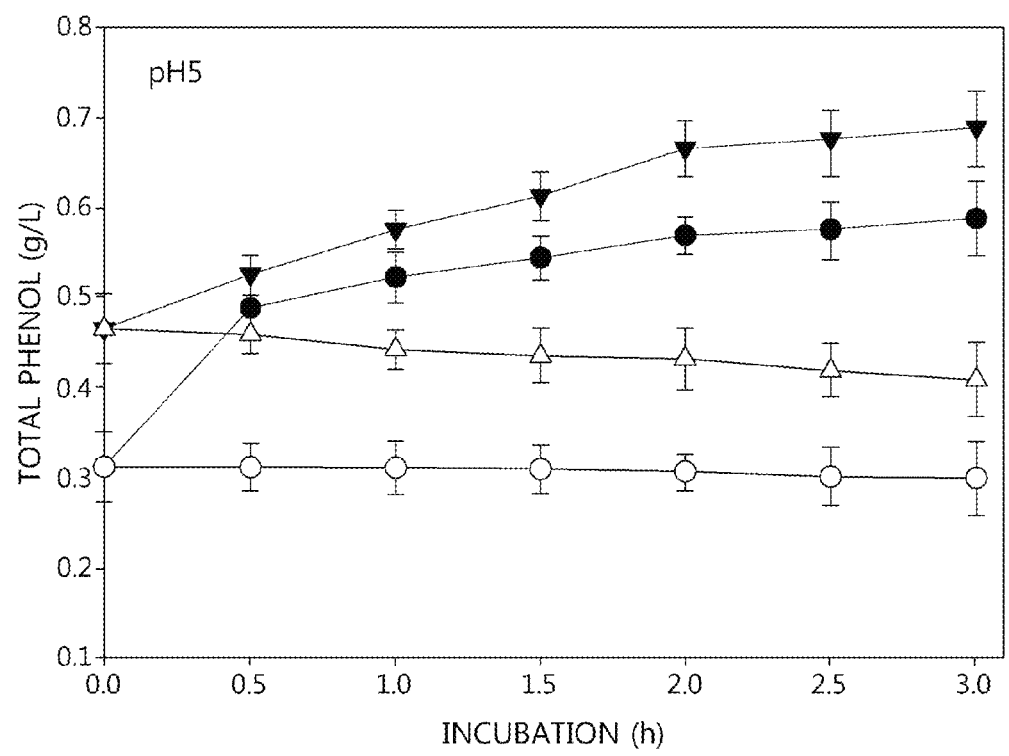
FIG. 9 is the result of measuring the change amounts of phenol contents by pH (pH 5) in an embodiment of the present invention.

The change amount of total phenol content included in the saccharficated product by the detoxification of the TcLac was measured with a Folin-Cilcalteu method, in which the principle of the color-development of a Folin-Cilcaltue reagent into a molybdenum blue as a result of reducing the reagent by the phenolic compound included in the saccharificated product is used. The results thereof are illustrated in FIGS. 7 to 9.

As illustrated in FIGS. 7 to 9, 15 U/mL of TcLac was treated into the biomass immersed during the detoxification according to Example, and the change amount of the total phenol content depending on the pH concentrations, 4, 4.5, and 5 in the reactant was measured. The total phenol content of rice straw (●), the total phenol content of rice straw after the simultaneous pretreatment and saccharification (SPS) (○), the total phenol content of willow (▼), and the total phenol content of willow after the simultaneous pretreatment and saccharification (SPS) (Δ) were compared according to the culturing times. As a result, it could be confirmed that for the total phenol content at pH 4.5, willow was decreased to be about 32.6% and rice straw was decreased to be about 49.8%.

For the present invention, a surfactant was used as a catalyst for improving the reactivity of a substrate during the saccharification of hydrolysis. The preferred surfactant may be a non-ionic surfactant, for example, polyoxyethylene sorbitan monolaurate (Tween-20) and polyoxyethylene sorbitan monooleate (Tween-80). In Example of the present invention, the products prepared by Sigma Aldrich (St. Louis, Mo., USA) were used as a non-ionic surfactant.

Figure 10:
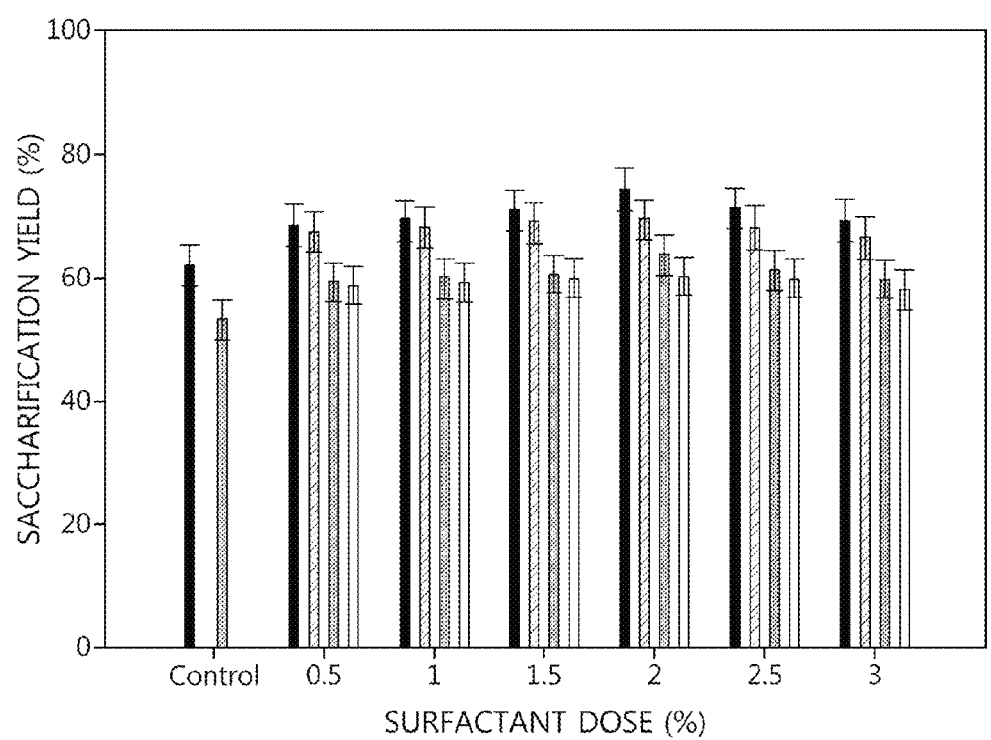
FIG. 10 is the result of the change of saccharification yield by a surfactant in an embodiment of the present invention.

FIG. 10 illustrates the change of saccharification yield depending on the use of surfactants according to Example of present invention. The rice straw and willow were immersed for all of the measuring samples, but were not subjected to a detoxification. Here, as a surfactant, Tween-20 and Tween-80 might be added in the amount of 0.5 to 3.0% (v/v).

As illustrated in a bar graph, the black color represents the result using rice straw and Tween-20, the gray dot represents the result using rice straw and Tween-80, the shaded represents the result using willow and Tween-20, and the white represents the result using willow and Tween-80.

As a result, it could be confirmed that in the case of adding 2% (v/v) of Tween-20, the saccharification yields (%) of the rice straw and willow were significantly increased to about 19.9% and 19.8%, respectively, as compared with a control group, exhibiting the highest saccharification yields. Therefore, preferably, a surfactant, Tween-20 might be added in the amount of 2.0% (v/v), and at this time, the saccharification yield was about 74.2±7.1%. At this time, when the contents of surfactant were 0.5% (v/v) and 1% (v/v), the saccharficiation yield to biomass was decreased due to the material inhibiting the enzyme function. On the contrary, when the surfactant was added to be higher than 2% (v/v), the saccharification yield might be decreased by inhibiting the catalytic reaction of enzyme.

In addition, as listed in Table 5, it could be confirmed that the final saccharification yields of rice straw and willow in the alkali-medicated sequential pretreatment and saccharification (SqPS) were about 75.4±7.1% and 64.5±6.6%, respectively, which were similar to the saccharification yield, 74.2±7.1%, when Tween-20 was added in the amount of about 2% (v/v) as a surfactant. In addition, it could be confirmed that the saccharification yields of the rice straw and willow in the simultaneous pretreatment and saccharification (SPS) were about 83.3% and 70.7%, respectively, which exhibited that the saccharficiation yields were improved to be high up to about 10.4% and 9.61%, respectively, as compared with the sequential pretreatment and saccharification (SqPS), Comparative Example.

The present invention includes fermenting the saccharificated products having reduced toxicity by the detoxificiation, and provides a method of preparing biofuel.

FIGS. 11 and 12 illustrate the change of the surface properties of biomass according to the detoxification using laccase and a physical treatment according to Example of the present invention, which are observed with an atomic force microscopy.

Using an atomic force microscopy (AFM), the degree of roughness was measured by contacting a fine AFM probe to the surface of biomass, and then, observing the shape of sample surface through the bending of the cantilever connected to the probe. Here, the force constant of stiffer cantilever was k=42 N/m and a flexural mode of the cantilever beam was the resonant frequency of about average 300 kHz.

As illustrated in FIGS. 11 and 12, the surface roughness of the biomass was measured by using largely three processes, in which 1 (raw RS or raw willow) represents the untreated biomass, 2 (RW or W) represents the biomass after being immersed, and 3 (DRS or DW) represents the biomass after the detoxification using laccase, and FIG. 10 used rice straw as biomass and FIG. 11 used willow as biomass.

In addition, in FIGS. 11 and 12, 'a' represents 3-D surface analysis, 'b' represents average surface roughness (ASR), and 'c' represents dark field surface analysis.

As a result, it could be confirmed that as listed in the following Table 8, for all the samples, the same areas were measured to be 10077.5 $\mu m^2$, and the roughness according to average surface roughness (ASR, $\mu m^2$) was about 0.257 my in the untreated raw RS sample, but was increased to be 5.51 mw in the RS after being immersed. In addition, it could be confirmed that the roughness was further increased to be 6.41 my after the detoxification, and thus, for the root mean square and ten point heights, the roughness values were increased after being immersed and the detoxification as compared with the untreated samples.

As the similar results, for willow, other biomass, it could be confirmed that the average surface roughness was increased, and the degree of the average surface roughness (ARS) of willow was low as compared with the rice straw. This was because willow had high content of lignin in a state of tree in the nature, and had the more closed cellulose and hemicelluloses.

TABLE 8

| Type of sample | Total area ($\mu m^2$) | Average roughness (mv) | Root mean square (mv) | Ten point height (mv) |
|---|---|---|---|---|
| raw RS | 10077.5 | 0.257 | 3.78 | 1.52 |
| RS | 10077.5 | 5.51 | 6.85 | 73.2 |
| DRS | 10077.5 | 6.41 | 7.14 | 76.2 |
| raw willow | 10077.5 | 0.312 | 4.12 | 2.24 |
| W | 10077.5 | 4.68 | 6.93 | 74.2 |
| DW | 10077.5 | 5.96 | 7.02 | 75.3 |

In Table 8, raw RS represents untreated rice straw, RS represents rice straw after being immersed, DRS represents rice straw after the detoxification, raw willow represents untreated willow, W represents willow after being immersed, and DW represents willow after the detoxification.

Therefore, it could be confirmed that the degradation was effectively performed by the influence of laccase of TcLac and lignocelluloses of the fungal consortium due to the simultaneous pretreatment and saccharification (SPS) of the present invention.

Meanwhile, as Comparative Example of the present invention, as illustrated in FIG. 1, the sequential pretreatment and saccharification (SqPS) was performed by sequentially performing the pretreatment, detoxification, and hydrolysis of the ground and immersed biomass, in which the washing was performed before the following process during each of the processes, and the sequential pretreatment and saccharification (SqPS) was performed at 85° C. using 0.1% w/v sodium hydroxide solution.

The saccharificated products without toxicity according to the present invention may be applied for the fermentation using all the microorganisms capable of producing yeast and bio alcohol, and thus, the bio chemical substances or biofuel may be prepared.

The fermentation according to an embodiment of the present invention may be performed by inoculating *Saccharomyces cerevisiae* (ATCC 32167 yeast), an ethanol fermenting yeast, in the amount of 2% v/v in a medium with the saccharificated products having reduced toxic materials or without toxic materials obtained through the simultaneous pretreatment and saccharification, and then, culturing the yeast in the medium at the temperature of 35° C. for 48 hours while being stirred at 90 to 110 RPM.

The medium for fermenting the hydrolysate (saccharificated products) includes 5 g/L of yeast extract, 10 g/L of ammonium sulfate (($NH_4)_2SO_4$), 4.5 g/L of $KH_2PO_4$, and 1.0 g/L of heptahydrated magnesium sulfate ($MgSO_4.7H_2O$), and has pH 5.0, and at this time, the pH may be adjusted with 1N hydrochloric acid (HCl) or 1 N sodium hydroxide (NaOH).

The medium after completing the culturing was centrifuged at the rate of 7500 g to obtain a supernatant, and then, the consumption amount of saccharificated products and the production amount of bioethanol in the supernatant might be measured.

For the fermentation yield according to an embodiment of the present invention, the quantitative analysis of the bioethanol produced from biomass was performed through a flame ionization detector (FID). Here, the measuring method of the flame ionization detector used air and hydrogen using Helium gas as a carrier gas, an initiating temperature was maintained to be 80° C., and then, the temperature was increased to be 190° C. After maintaining 190° C. for 10 minutes, the measurement was performed to measure the concentration of bioethanol (g/L).

Figure 13:
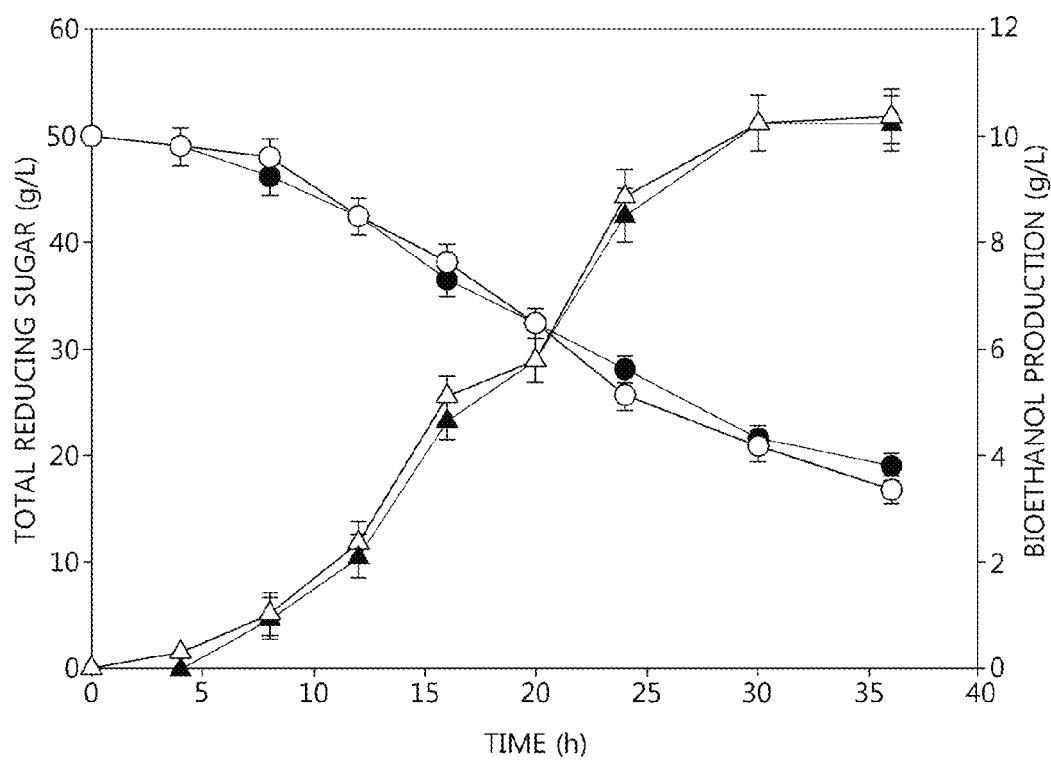
FIG. 13 illustrates the total amount of reducing sugar (g/L) and the production amount of bioethanol (g/L) by the fermentation process as an embodiment of the present invention.

FIG. 13 is the graph illustrating the result of the fermentation yield according to an embodiment of the present invention, illustrating the total amount of used reducing sugar (g/L) and the amount of produced bioethanol (g/L). The amount of reducing sugar (●) by the sequential pretreatment and saccharification (SqPS), the amount of reducing sugar (○) by the simultaneous pretreatment and saccharification (SPS), the amount of bioethanol (Δ) by the sequential pretreatment and saccharification (SqPS), and the amount of bioethanol (▲) by the simultaneous pretreatment and saccharification (SPS) were compared with the culturing time.

As illustrated in drawings, it could be confirmed that the production amount of bioethanol in rice straw was about 0.52 g/L/h per a hour and the production amount of the final bioethanol was 10.2 g/L, which exhibited that as compared with the sequential pretreatment and saccharification (SqPS), the sugar conversion (%), in which sugar was converted into bioethanol, was 72.4%, through the simultaneous pretreatment and saccharification (SPS) of the present invention, exhibiting high sugar conversion.

In general, for the method of performing the pretreatment and saccharification, separately, in the case of using 1 kg of a substrate, the washing should be performed before the following process, and at this time, the washing requires 50 L clear water, generally. However, according to the present invention, the washing is not required, and the method can be performed, simultaneously, and thus, biofuel can be produced from biomass, rapidly, economically, and eco-friendly.

[Accession Number]
Accession organization: Korean Culture Center of Microorganisms (Foreign country)
Accession number: KCCM11186P
Accession date: 2011 Apr. 20
Accession organization: Korean Culture Center of Microorganisms (Foreign country)
Accession number: KCCM11187P
Accession date: 2011 Apr. 20

According to the present invention, the enzyme produced from a fungal consortium has an effect on producing saccharificated products from biomass in excellent saccharification yield as compared with the conventional saccharification enzyme.

In addition, the toxicity of the toxic materials that may be produced from the decomposition of biomass by performing the simultaneous pretreatment and saccharification process, especially, a phenolic compound, can be reduced or removed through laccase by performing a biological treatment process.

Therefore, it is possible to omit the washing process during the pretreatment and saccharification process. Accordingly, the complexity of the detoxification process and the loss of sugar can be solved, and biofuel can be produced from biomass, rapidly, economically, and eco-friendly.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of simultaneous pretreatment and saccharification of biomass, comprising a first step of pulverizing biomass and immersing the pulverized biomass; and a second step of preparing saccharificated products by performing the simultaneous pretreatment and saccharification of the immersed biomass with an enzyme produced by inoculating a fungal consortium in a culture medium and culturing the fungal consortium,
  wherein the second step further includes reducing or removing toxic materials through laccase produced by culturing with a strain producing laccase, in which the strain producing laccase is *Tyromyces chioneus*;
  wherein the fungal consortium includes *Pholiota adiposa* and *Armillaria gemina*; and
  wherein the enzyme is any one selected from the group consisting of xylanase, endoglucanase (EG), β-glucosidase (BGL), and cellobiohydrolase (CBH).

2. The method of simultaneous pretreatment and saccharification of biomass of claim 1, wherein the second step further includes adding a surfactant.

3. The method of simultaneous pretreatment and saccharification of biomass of claim 2, wherein the surfactant is any one selected from the group consisting of polyoxyethylene sorbitan monolaurate (Tween-20) and polyoxyethylene sorbitan monooleate (Tween-80).

4. The method of simultaneous pretreatment and saccharification of biomass of claim 1, wherein the *Pholiota adiposa* and *Armillaria gemina* are mixed in the weight ratio (w/w) of 1:2, and then, are inoculated into a culturing medium.

5. The method of simultaneous pretreatment and saccharification of biomass of claim 1, wherein the fungal consortium is cultured at a temperature of 20° C. to 30° C. and a culturing medium pH of 4 to 6.5.

6. The method of simultaneous pretreatment and saccharification of biomass of claim 1, wherein the fungal consortium is cultured at a stirring rate of the culturing medium of 50 RPM to 300 RPM for 36 hours to 48 hours.

7. A method of preparing bioethanol, the method comprising fermenting saccharificated products prepared by the method of claim 1,
  wherein the fermentation is performed by inoculating a fermentation strain into the saccharificated products prepared.

8. The method of claim 7, wherein the fermentation strain is yeast, *Saccharomyces cerevisiae*.

9. The method of claim 7, wherein the fermentation strain is cultured at the temperature of 35° C. and pH of 5 for 48 hours while being stirred at 90 to 110 RPM.

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
tccgtaggtg aacctgccg                                              19

<210> SEQ ID NO 2
<211> LENGTH: 20

-continued

```
<212> TYPE: DNA
<213> ORGANISM: Artificial Sequence
<220> FEATURE:
<223> OTHER INFORMATION: primer

<400> SEQUENCE: 2
tcctccgctt attgatatgc                                          20
```